(12) United States Patent
Barrett et al.

(10) Patent No.: US 8,624,199 B2
(45) Date of Patent: Jan. 7, 2014

(54) SAMPLE BLOCK HOLDER

(75) Inventors: Matthew Barrett, Narangba (AU); Michael D. Smith, New Farm (AU); Michal Geryk, Brno (CZ); Paul Scagnetti, New Farm (AU); Richard Tovey, Acacia Ridge (AU)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/284,729

(22) Filed: Oct. 28, 2011

(65) Prior Publication Data
US 2013/0105677 A1 May 2, 2013

(51) Int. Cl.
H01J 37/28 (2006.01)
H01J 37/16 (2006.01)

(52) U.S. Cl.
USPC ................................. 250/442.11; 250/440.11

(58) Field of Classification Search
USPC ............. 250/440.11, 442.11, 252.1; 269/900, 269/902; 378/79; 73/864.83, 864.84, 73/864.85, 864.91
See application file for complete search history.

(56) References Cited

U.S. PATENT DOCUMENTS

| | | | |
|---|---|---|---|
| 4,136,429 A | 1/1979 | Brandes | |
| 4,242,586 A | 12/1980 | Warble | |
| 4,435,507 A | 3/1984 | Stenkvist | |
| 4,834,943 A | 5/1989 | Yoshiyama | |
| 5,043,144 A * | 8/1991 | Gordon et al. | 422/561 |
| RE35,514 E | 5/1997 | Albrecht et al. | |
| 6,002,136 A * | 12/1999 | Naeem | 250/442.11 |
| 6,093,930 A | 7/2000 | Boyette, Jr. et al. | |
| 6,888,920 B2 | 5/2005 | Blank et al. | |
| 7,597,852 B2 * | 10/2009 | Desrosiers et al. | 422/534 |
| 2004/0008814 A1 * | 1/2004 | Shafer | 378/79 |
| 2005/0060868 A1 * | 3/2005 | McMurtry | 29/559 |
| 2006/0051251 A1 * | 3/2006 | Desrosiers et al. | 422/102 |
| 2008/0250881 A1 * | 10/2008 | Dona | 73/864.91 |
| 2010/0060893 A1 | 3/2010 | Norton et al. | |
| 2011/0133083 A1 * | 6/2011 | Bierhoff et al. | 250/310 |

FOREIGN PATENT DOCUMENTS

| | | |
|---|---|---|
| JP | 05-087707 | 4/1993 |
| JP | 10-312763 | 11/1998 |
| JP | 2001-006597 | 1/2001 |
| JP | 2011-113640 | 6/2011 |
| JP | 2011113640 A * | 6/2011 |

OTHER PUBLICATIONS

Oversluizen, T. et al., "Kinematic mounting systems for National Synchrotron Light Source beamlines and experiments" Rev. Sci. Instrum. 63 (1), Jan. 1992.*

(Continued)

*Primary Examiner* — David A Vanore
*Assistant Examiner* — Wyatt Stoffa
(74) *Attorney, Agent, or Firm* — Scheinberg & Associates, PC; Michael O. Scheinberg

(57) ABSTRACT

A sample holder assembly includes a sample tray, a base plate, a stage mount, and a calibration standard mounted onto the stage mount. Three mating structures on the bottom of the base plate mate with corresponding structures on a stage mount that is attached to the sample stage of the SEM. An optional contacting conductor provides electrical contact between the stage mount and the base plate so that charge generated on the sample by the electron beam can leave the sample through the sample conductive layer to the sample tray, to the base plate, to the stage mount, and through the grounded stage.

20 Claims, 4 Drawing Sheets

(56) References Cited

OTHER PUBLICATIONS

Furse, J.E., "Kinematic design of fine mechanisms in instruments," J. Phys. E: Sci. Instrum, 1981, pp. 264-272, vol. 14.

Hale, Layton C., et al., "Optimal design techniques for kinematic couplings," Journal of the International Societies for Precision Engineering and Nanotechnology, Oct. 5, 2000, pp. 114-127, vol. 25.

Lapicki, Adam, et al., "Kinematic sample mounting system for accurate positioning of transferrable samples," J. Vac. Sci. Technol., Sec. A, Sep./Oct. 2000, pp. 2603-2605, vol. 18 (5).

Miller, Jeff, "Jeff's (Fairly Comprehensive) Raith Usage Notes," Marcus Group, Harvard University, Unknown date, Version 20040929.1.

Oversluizen, Tom, et al., "Kinematic mounting systems for National Synchrotron Light Source beamlines and experiments," Rev. Sci. Instrum., Jan. 1992, pp. 1285-1288, vol. 63 (1).

Unknown, "Raith e_LiNE User Guide," Nov. 2009, 18 pages.

Slocum, A.H., "Kinematic couplings for precision fixturing—Part I: Formulation of design parameters," Precision Engineering, 1988 Butterworth & Co. (Publishers) Ltd, pp. 85-88.

Slocum, A.H. et al., "Kinematic couplings for precision fixturing—Part 2: Experimental determination of repeatability and stiffness," Precision Engineering, Jul. 1988 Butterworth & Co. (Publishers) Ltd, pp. 115-122, vol. 10 No. 3.

Slocum, Alexander H., "Design of three-groove kinematic couplings," Precision Engineering, Apr. 1992, pp. 67-76, vol. 14 No. 2.

Slocum, Alexander, "Kinematic couplings: A review of design principles and applications," International Journal of Machine Tools & Manufacture, Oct. 20, 2009, pp. 310-327, vol. 50.

Zelenika, S. et al., "Kinematic Couplings for Synchrotron Radiation Instrumentation," 2nd International Workshop on Mechanical Engineering Design of Synchrotron Radiation Equipment and Instrumentation, Sep. 5-6, 2002, pp. 262-270.

Gottlieb, Paul, 'Automated sample preparation,' U.S. Appl. No. 61/478,351, filed Apr. 22, 2011.

* cited by examiner

SAMPLE BLOCK HOLDER

TECHNICAL FIELD OF THE INVENTION

The present invention relates to a sample holder for mineralogical samples for x-ray spectroscopic analysis.

BACKGROUND OF THE INVENTION

Mineral analysis systems, such as the Qemscan and MLA from FEI Company, have been used for many years to determine minerals present in mines in order to determine the presence of valuable minerals. Such systems direct an electron beam toward the sample and measure the energy of X-rays coming from the material in response to the electron beam. One such process is called "energy dispersive x-ray analysis" or "EDS," which can be used for elemental analysis or chemical characterization of a sample.

In EDS analysis, a high-energy beam of charged particles such as electrons or protons, or a beam of X-rays, is focused into the sample being studied to stimulate the emission of X-rays from the sample. The energy of the X-rays emitted from a specimen is characteristic of the atomic structure of the elements making up the specimen. By measuring the number and energy of the X-rays emitted from a specimen using an energy-dispersive spectrometer and comparing the measured spectra to a library of reference spectra of known compositions, the unknown elemental composition of the specimen can be determined. EDS analysis, especially when coupled with back-scattered electron (BSE) analysis, can also be used to quantify a wide range of mineral characteristics, such as mineral abundance, grain size, and liberation. Mineral texture and degree of liberation are fundamental properties of ore and drive its economic treatment, making this type of data invaluable to geologists, mineralogists, and metallurgists who engage in process optimization, mine feasibility studies, and ore characterization analyses.

Mineral analysis systems of this type are also used in the oil and gas industry, as well as mines. Drill cuttings (drill bit-induced rock chips) and diamond drill cores can be analyzed to allow geologists to determine the exact nature of the material encountered during drilling, which in turn allows more accurate predictions as to the material still ahead of the drill, thus reducing risk in exploration and production. During drilling, a liquid referred to as "mud" is injected into the well to lubricate the drill and return the cuttings out of the well. A sample can be taken from the mud that includes cuttings from the drill. Great importance is often placed on documenting cuttings and cores as accurately as possible, both at the time of drilling and post-drilling. Characterizing down-hole lithological variation in a reservoir sequence is a critical requirement in exploration wells and production wells, and mineralogical and petrographic studies underpin the fundamental understanding of reservoir and seal characteristics. Traditional optical, scanning electron microscope (SEM), electron probe microanalysis (EPMA), and X-ray diffraction (XRD) analysis methods are well established and widely used within the industry.

Samples for use in analytical instruments such as Qemscan and MLA systems are prepared so that the material to be analyzed is presented to the instrument as a flat, carbon coated surface within a sample block, typically 30 mm in diameter. Material to be analyzed, such as material retrieved from a mine, is carefully sampled from the mine, crushed, and mixed with epoxy in a mold. The sample is cured and then the sample block is removed. The sample block is ground and polished to expose the interior of some of the particles and to produce a smooth surface. The surface is coated with a carbon film to form a conductive coating to prevent electrical charging by the electron beam.

The sample block is then placed into a sample holder and clamped in place. Exchange of the older style sample holders requires operator skill and an understanding of the mating surfaces, careful alignment conducted by eye and, in some instances, use of a tool. Manually aligning by operator eye can be difficult and is a frequent source of error. If the sample holder is not seated and aligned correctly, which can only be confirmed by completing system set up, the whole process may need to be redone. That is, the beam is turned off, the vacuum chamber vented, and the sample holder removed and re-installed. A less experienced operator may fail to recognize that the sample holder is misaligned and make faulty measurements, losing many hours of work.

Once the sample holder block is correctly positioned, the calibration points need to be re-entered into the software by the operator using both the SEM software controls and manual manipulation of the sample stage. This operation requires a clear understanding of the set up process and the knowledge and ability to complete a stage rotation alignment. The process relies on operator skill and is not readily automated. It would be preferable to have a system that is fast, repeatable, does not require a skilled operator, and is susceptible to automation.

SUMMARY OF THE INVENTION

An object of the invention is to provide a sample holder that facilitates mineralogy applications in the field.

In a preferred embodiment, a sample holder assembly includes a sample tray, a base plate, a stage mount, and a calibration standard mounted onto the stage mount. Three mating structures on the bottom of the base plate mate with corresponding structures on a stage mount that is attached to the sample stage of the SEM. An optional contacting conductor provides electrical contact between the stage mount and the base plate so that charge generated on the sample by the electron beam can leave the sample through the sample conductive layer to the sample tray, to the base plate, to the stage mount, and through the grounded stage.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Charged particle beam systems for mineral analysis are preferably rugged for use in the field near a mine or a well site. SEMS intended for use in the field are preferably adapted to be used by less skilled technicians and for automation. Such design attributes are also beneficial for SEMS used in laboratories. The alignment of the sample holder is preferably simple, precise, quick, and easily automated.

A common issue in automated mineralogy is the inability of the beam to automatically return to previously set calibration points for automated system calibration and to return to sample locations for measurement after a sample exchange. If the calibration standard is positioned in the sample holder and removed with the sample holder, the sample holder must be carefully aligned in on the sample stage so that the calibration standard is positioned in a known location with respect to the beam. If the alignment is not correct, the beam will impact at a different point on the calibration sample each time, which could result in erroneous calibration and measurements.

A preferred robust sample holder system of the present invention ensures precise and repeatable sample and calibration standard positioning and provides that the calibration and sample locations cannot be influenced by differences between operator skill levels. A preferred embodiment allows for greater accuracy and speed in manual operation and for automation by improving the ease of use of the sample holder. Preferred embodiments provide an easier, faster sample exchange process with precise repeatable locating of calibration standards and samples without operator influence on positioning at sample exchange.

In preferred embodiments, the stage-to-sample holder assembly interface uses complementary aligning structures, such as ball and cone locating interfaces, on the sample holder assembly and the stage mount to locate and orient the sample holder relative to the stage or a stage mount mounted onto the stage. The calibration standard remains on the SEM stage as the sample holder is removed and replaced. The calibration standard provides the operator with a visual locator for correct orientation of sample holder assembly.

Figure 1:
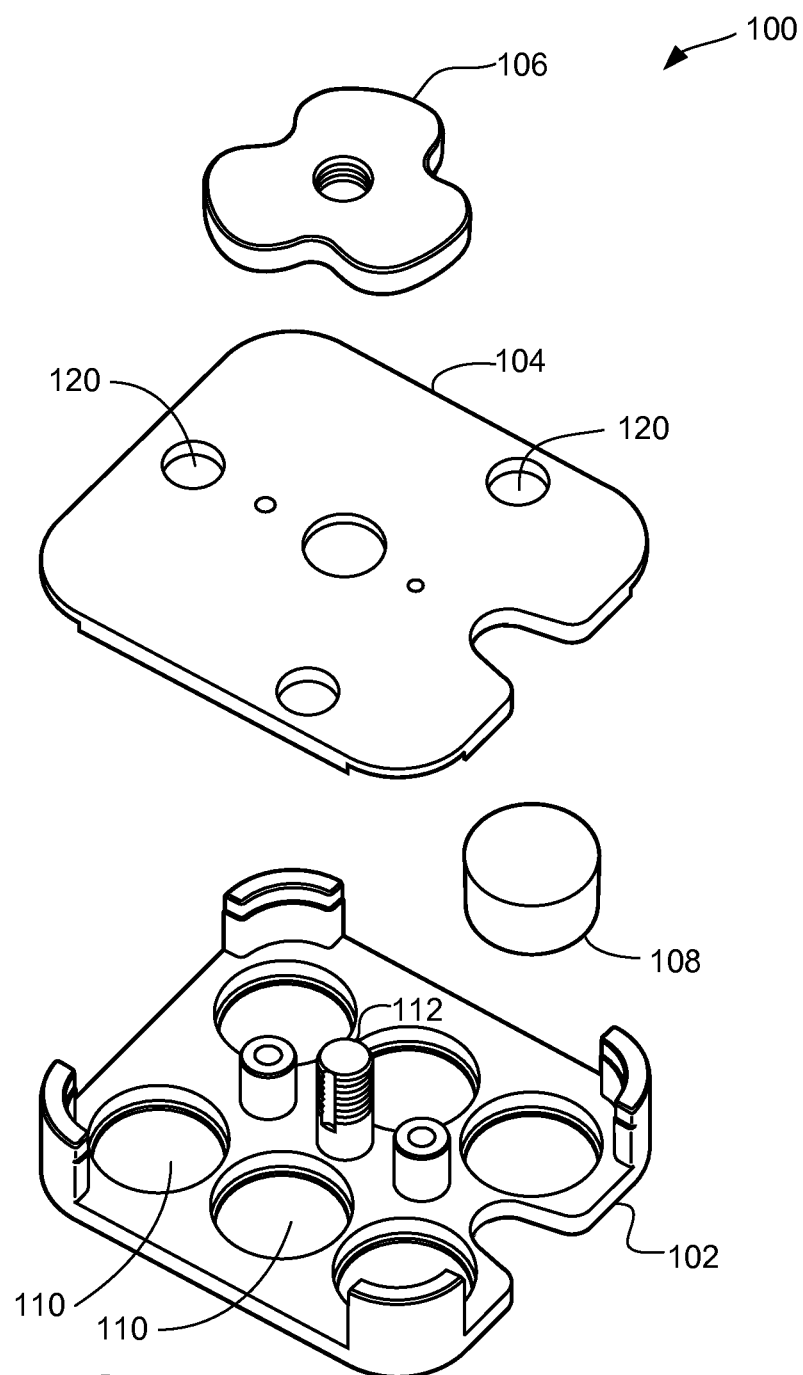
FIG. 1 is an exploded view of a sample holder assembly embodying the present invention.

FIG. 1 shows an exploded view of a preferred sample holder assembly 100 including a sample tray 102, a base plate 104, and a knob 106 that secures the sample tray 102 to the base plate 104 by screwing onto shaft 106 extending from the sample tray 102. Multiple sample blocks 108 (one shown) are positioned at the six holes 110 in sample tray 102 and are secured between the sample tray 102 and the base plate 104 when the knob 106 is threaded onto a post 112 extended from sample tray 102 through base plate 104. Base plate 104 includes conical indentation 120 to mate with corresponding mating structures on a stage mount as described below. Knob 106 allows sample holder assembly 100 to be assembled rapidly by an operator without the use of tools, such as screwdrivers.

Figure 2:
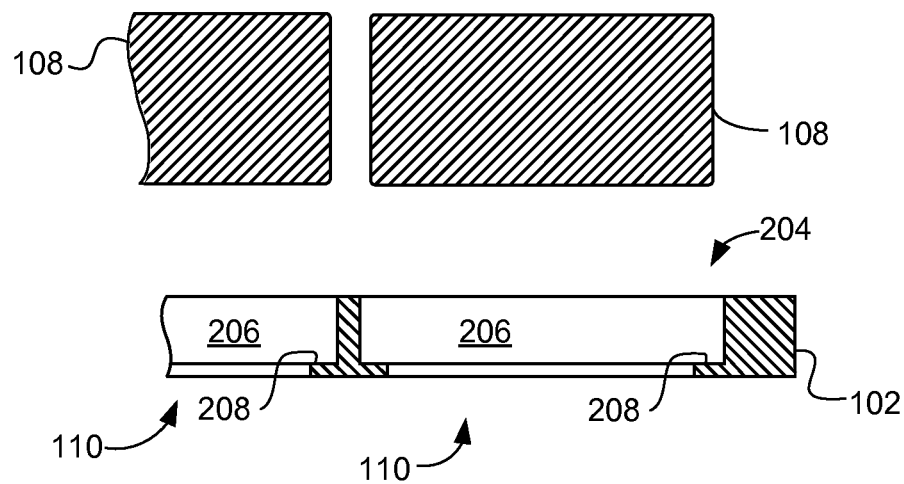
FIG. 2 shows a detail of the sample tray component of the sample holder assembly of FIG. 1.
Figure 3:
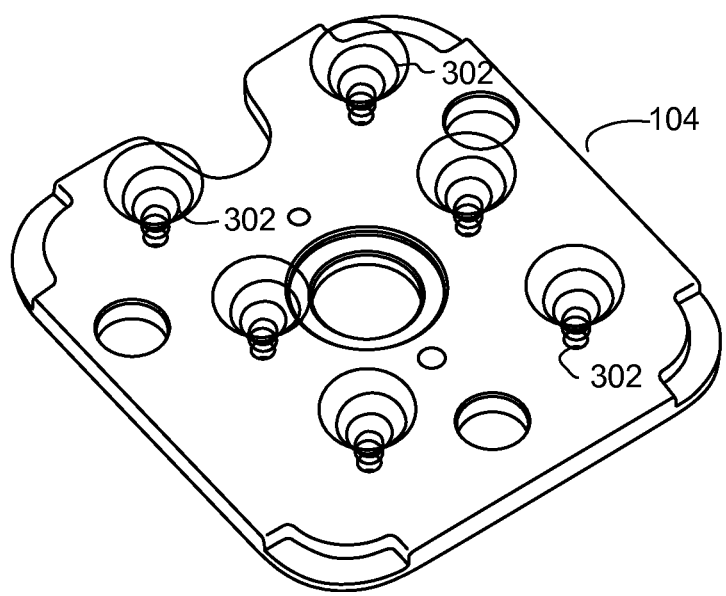
FIG. 3 shows a top view of the base plate of the sample holder assembly of FIG. 1.

FIG. 2 shows a detail of the edge of the hole in sample tray 102. Each sample hole 110 includes a counterbore 204 that provides an indentation 206 that positions the sample block 108 and provides a lip 208 having a diameter smaller than that of the sample block to prevent the sample block from passing through the hole. FIG. 3 shows a top view of the base plate 104, showing springs 302 that press the sample blocks 108 against the lip 208 to orient the sample at a known and repeatable position in relation to the base plate. The springs or other biasing means ensures the sample surfaces are flat, normal to the beam, and held at a known working distance from the column, as well as to ensure a good electrical contact to allow electrical charges to drain from the sample block 108 to the sample tray 102.

Figure 4:
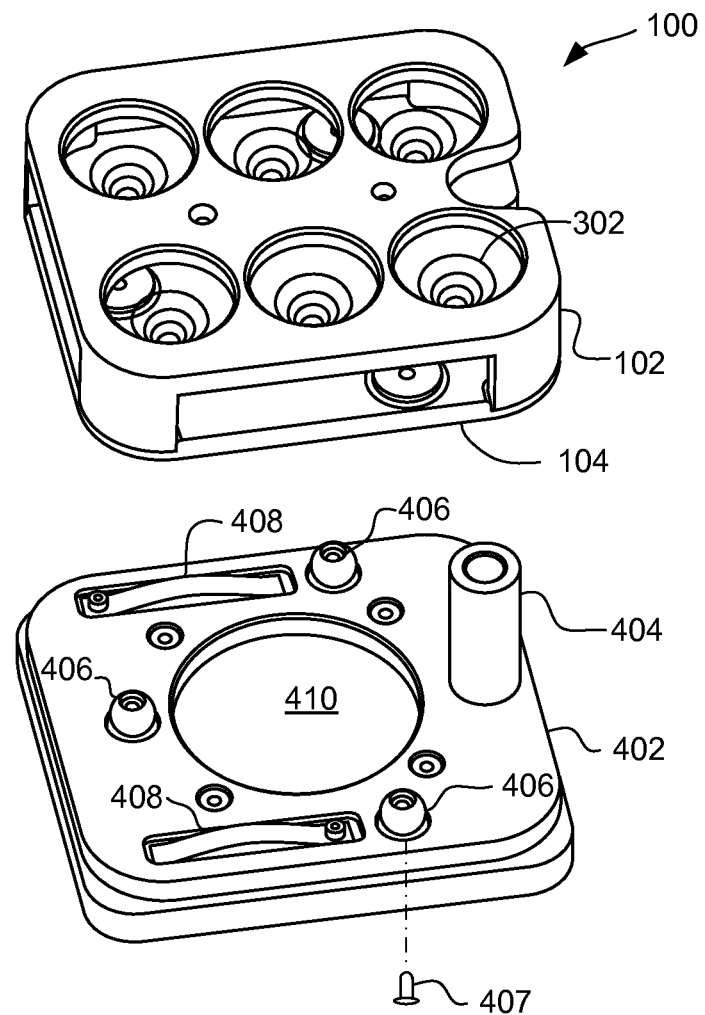
FIG. 4 is an exploded view showing the sample holder assembly being placed onto the stage mount.

FIG. 4 shows sample holder assembly 100 (without sample blocks) being positioned onto stage mount 402. Stage mount 402 is secured to a moveable stage (not shown) for a charged particle beam system. A calibration standard holder, such as a calibration column 404, is secured to the stage mount 402. Hemispherical structures 406 mounted using corresponding fasteners 407 (one shown) onto stage mount 402 provide mating structures for the conical indentations in the bottom of the base plate 104. Biasing means, such as leaf springs 408, provide electrical contact between the stage mount 402 and the sample holder assembly 100. The tension in leaf springs 408 is sufficient to provide electrical contact, but not sufficient to prevent seating of the conical indentations of sample holder 100 fully onto the hemispherical mating surfaces of stage mount 402. Sample holder assembly 100 rests on stage mount 402 without being clamped during operation, with the weight alone of sample holder assembly 100 maintaining the contact between the aligning structures in the sample holder assembly and the aligning structures in the stage mount, therefore maintaining the sample holder in the proper position and orientation. Aperture 410 accommodates knob 106 (FIG. 1) protruding from sample holder assembly 100.

Figure 5:
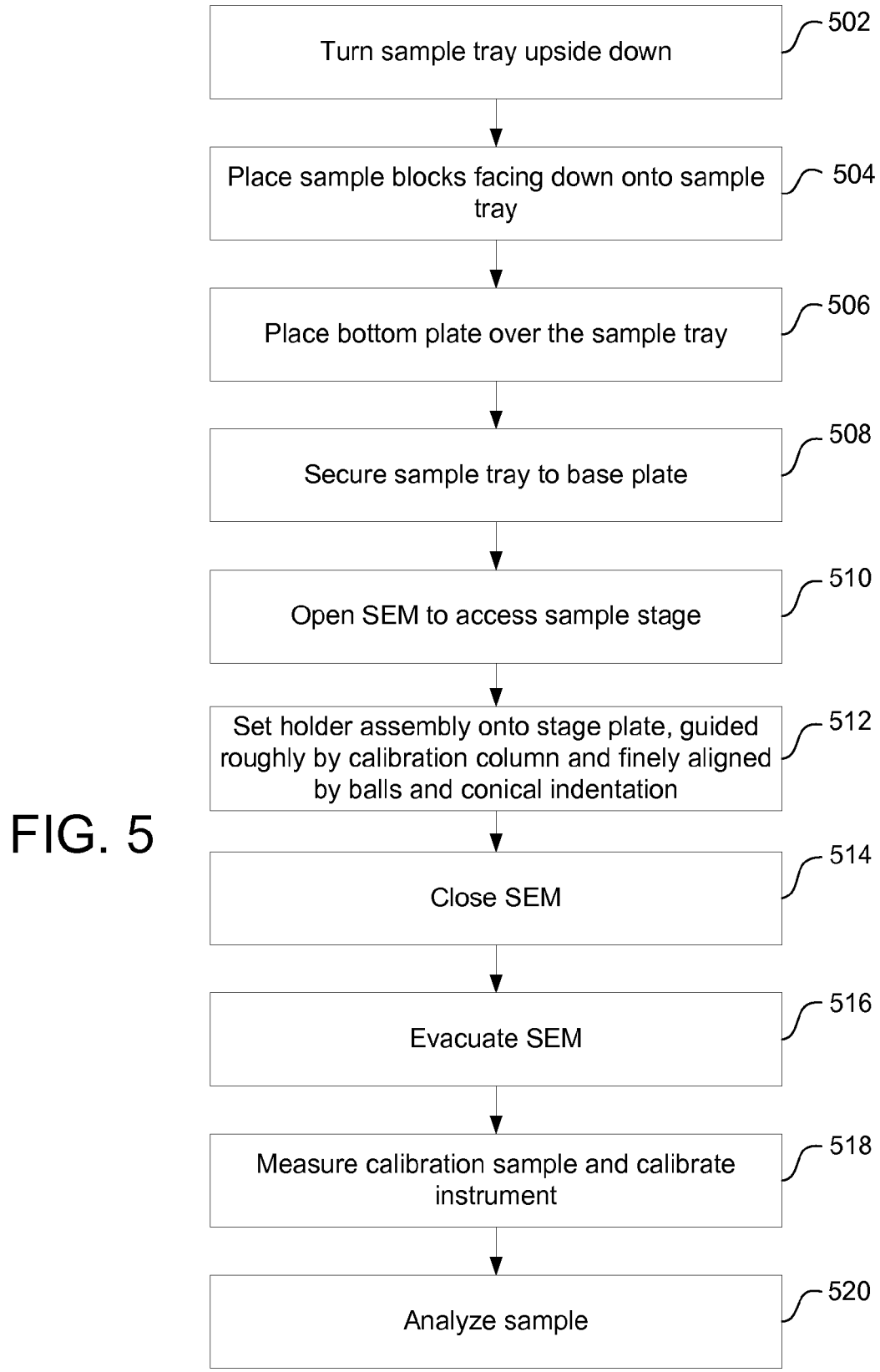
FIG. 5 is a flow chart showing the preferred steps of using an embodiment of the invention.

FIG. 5 is a flow chart showing a method of using a sample holder. The sample holder assembly is loaded by turning the sample tray upside down in step 502 and in step 504, the sample blocks are placed facing down into the sample tray with the sample at one or more of the hole locations. Each hole location includes a counterbore that provides an indentation that positions the sample block and provides a lip having a diameter smaller than that of the sample block to prevent the sample block from passing through the hole. The bottom plate is then placed over the sample tray in step 506. The bottom plate includes a biasing means, such as a spring, at each of the sample block locations to press the sample block against the lip, thereby positioning the top of the sample block at a consistent, known height above the bottom of the sample holder assembly, which assists in rapidly focusing the electron beam. By pressing the sample block into the lip, the spring also ensures a good electrical contact between the conductive top of the sample block and the sample tray.

The base plate is then secured against the sample tray in step 508, for example, by threading a knob nut onto a shaft extending from the sample tray extending through the base plate. The knob can be easily threaded onto and off of the shaft of the sample tray to rapidly change sample blocks by hand, without the use of tools. Other types of quick clamping devices may also be used to secure the sample tray to the base plate.

The base plates include three conical indentations. The indentations are preferably manufactured separately and pressed into the base plate. The stage mount includes three hemispherical structures that mate with the three conical indentations on the bottom of the base plate. In step 510, the SEM is opened to provide access to the stage mount. In step 512, the sample holder assembly is set onto the stage mount, with the calibration cylinder fitting into a notch in the sample holder assembly to provide rough positioning of the sample holder assembly, with the rough positioning being sufficiently close so that the hemispherical structures on the stage mount will self align with the conical indentation in the conical indentations to produce a fine alignment. The aligning structures on the base plate and stage mount preferably constrain the sample assembly in six degrees of freedom. The orientation and height of the sample holder assembly, as well as the position, is determined by the aligning structures. Thus, precise positioning facilitates automation by facilitating automatic focusing to the known height. The final stages of using the device are as follows: close the SEM 514, evacuate the SEM 516, measure calibration sample and calibrate instrument 518, and analyze sample 520. As will be recognized, the use of three conical indentations and three hemispherical structures overconstrains the sample holder assembly in three dimensions. The use of identical indentation and hemispherical structure reduces manufacturing costs, while the overconstraint does not decrease the precision to below an acceptable level. Maintaining the calibration standard in the sample chamber facilitates automation by providing a consistent position for the calibration standard, which position does not change as the samples are loaded and unloaded.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A sample holder system for a charged particle beam system having a sample chamber with a sample stage, comprising:
   a stage mount for being affixed to the stage of a charged particle beam system, the stage mount including three alignment structures;
   a base plate including three alignment structures, each alignment structure on the base plate structured to mate with a corresponding alignment structure on the stage mount, one of each mating alignment structures on the base plate or on stage mount including a hemispherical portion;
   a sample tray configured to be removably attachable onto the base plate, the sample tray having multiple holes for positioning sample blocks;
   a clamp holding the sample tray to the base plate;
   a calibration standard holder secured to the stage mount and remaining on the stage mount as samples are changed in the charged particle beam system; and
   springs positioned on the base plate to press the sample blocks into the sample tray and to repeatably orient the sample blocks relative to the sample tray.

2. The sample holder system of claim 1 in which the alignment structures that mate with the three hemispherical portions comprise conical indentations.

3. The sample holder system of claim 1 in which the alignment structures that mates with the three alignment structures on the stage mount comprise hemispherical portions and in which the three alignment structures on the base plate comprise conical or hemispherical indentations.

4. The sample holder system of claim 1 in which the combined sample tray and base plate holder with sample blocks is maintained on the sample stage during charged particle beam operation by the weight of the sample holder, without additional restraint.

5. The sample holder system of claim 1 in which the three mating structures on the stage mount are attached to the stage mount using fasteners.

6. A sample holder system for a charged particle beam system having a sample chamber with a sample stage, comprising
   a stage mount for being affixed to the stage of a charged particle beam system, the stage mount including three alignment structures;
   a base plate including three alignment structures, each alignment structure on the base plate structured to mate with a corresponding alignment structure on the stage mount, one of each mating alignment structures on the base plate or on stage mount including a hemispherical portion;
   a sample tray configured to be removably attachable onto the base plate, the sample tray having multiple holes for positioning sample blocks;
   a clamp holding the sample tray to the base plate;
   a calibration standard holder secured to the stage mount and remaining on the stage mount as samples are changed in the charged particle beam system; and
   springs positioned on the stage mount to ensure electrical contact between the stage mount and the base plate, the springs providing sufficient biasing force to provide electrical contact while still allowing the weight of the sample tray, base plate, and sample blocks to cause the aligning structures to fully engage.

7. The sample holder system of claim 6 in which the alignment structures that mate with the three hemispherical portions comprise conical indentations.

8. The sample holder system of claim 6 in which the alignment structures that mates with the three alignment structures on the stage mount comprise hemispherical portions and in which the three alignment structures on the base plate comprise conical or hemispherical indentations.

9. The sample holder system of claim 6 in which the combined sample tray and base plate holder with sample blocks is maintained on the sample stage during charged particle beam operation by the weight of the sample holder, without additional restraint.

10. The sample holder system of claim 6 in which the three mating structures on the stage mount are attached to the stage mount using fasteners.

11. A sample holder system for a charged particle beam system having a sample chamber with a sample stage, comprising:
    a stage mount for being affixed to the stage of a charged particle beam system, the stage mount including three alignment structures;
    a base plate including three alignment structures, each alignment structure on the base plate structured to mate with a corresponding alignment structure on the stage mount;
    a sample tray configured to be removably attachable onto the base plate, the sample tray having multiple sample blocks positions;
    a calibration standard holder secured to the stage mount and remaining on the stage mount as samples are changed in the charged particle beam system; and springs positioned on the base plate to press the sample blocks into the sample tray and to repeatably position the sample blocks relative to the sample tray.

12. The sample holder system of claim 11 in which the alignment structures or the corresponding alignment structures include three hemispherical portions or conical indentations.

13. The sample holder system of claim 11 in which the alignment structures that mates with the three alignment structures on the stage mount comprise hemispherical portions and in which the three alignment structures on the base plate comprise conical or hemispherical indentations.

14. The sample holder system of claim 11 in which the combined sample tray and base plate holder with sample blocks is maintained on the sample stage during charged particle beam operation by the weight of the sample holder, without additional restraint.

15. The sample holder system of claim 11 in which the three mating structures on the stage mount are attached to the stage mount using fasteners.

16. A sample holder system for a charged particle beam system having a sample chamber with a sample stage, comprising:
   a stage mount for being affixed to the stage of a charged particle beam system, the stage mount including three alignment structures;
   a base plate including three alignment structures, each alignment structure on the base plate structured to mate with a corresponding alignment structure on the stage mount;
   a sample tray configured to be removably attachable onto the base plate, the sample tray having multiple sample blocks positions;
   a calibration standard holder secured to the stage mount and remaining on the stage mount as samples are changed in the charged particle beam system; and
   springs positioned on the stage mount to ensure electrical contact between the stage mount and the base plate, the springs providing sufficient biasing force to provide electrical contact while still allowing the weight of the sample tray, base plate, and sample blocks to cause the aligning structures to fully engage.

17. The sample holder system of claim 16 in which the alignment structures or the corresponding alignment structures include three hemispherical portions or conical indentations.

18. The sample holder system of claim 16 in which the alignment structures that mates with the three alignment structures on the stage mount comprise hemispherical portions and in which the three alignment structures on the base plate comprise conical or hemispherical indentations.

19. The sample holder system of claim 16 in which the combined sample tray and base plate holder with sample blocks is maintained on the sample stage during charged particle beam operation by the weight of the sample holder, without additional restraint.

20. The sample holder system of claim 16 in which the three mating structures on the stage mount are attached to the stage mount using fasteners.

* * * * *